US010589015B2

(12) United States Patent
Bartlett et al.

(10) Patent No.: US 10,589,015 B2
(45) Date of Patent: Mar. 17, 2020

(54) GATED-CONCENTRIC ARTIFICIAL LUNG

(71) Applicant: THE REGENTS OF THE UNIVERSITY OF MICHIGAN, Ann Arbor, MI (US)

(72) Inventors: Robert H. Bartlett, Ann Arbor, MI (US); Joseph L. Bull, Ann Arbor, MI (US); Uditha Piyumindri Fernando, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 181 days.

(21) Appl. No.: 15/519,760

(22) PCT Filed: Oct. 19, 2015

(86) PCT No.: PCT/US2015/056177
§ 371 (c)(1),
(2) Date: Apr. 17, 2017

(87) PCT Pub. No.: WO2016/064715
PCT Pub. Date: Apr. 28, 2016

(65) Prior Publication Data
US 2017/0258978 A1 Sep. 14, 2017

Related U.S. Application Data

(60) Provisional application No. 62/065,790, filed on Oct. 20, 2014.

(51) Int. Cl.
*A61M 1/16* (2006.01)
*B01D 63/02* (2006.01)

(52) U.S. Cl.
CPC ........... *A61M 1/1698* (2013.01); *B01D 63/02* (2013.01); *A61M 2206/10* (2013.01); *B01D 2313/08* (2013.01)

(58) Field of Classification Search
CPC ............ A61M 1/1698; A61M 2206/10; B01D 2313/08; B01D 63/02
See application file for complete search history.

(56) References Cited

U.S. PATENT DOCUMENTS 3,862,031 A 1/1975 Leonard
4,111,659 A 9/1978 Bowley
(Continued)

FOREIGN PATENT DOCUMENTS

EP 0187708 B1 8/1992
JP H08182758 A 7/1996
KR 102014007335 A 6/2014

OTHER PUBLICATIONS

International Search Report and Written Opinion for PCT/US2015/056177, dated Jan. 25, 2016; ISA/KR.
(Continued)

*Primary Examiner* — Leslie R Deak
(74) *Attorney, Agent, or Firm* — Harness, Dickey & Pierce, P.L.C.

(57) ABSTRACT

An artificial lung including a housing having a circular outer wall being enclosed by a first surface and a second surface to define an interior volume, a blood inlet port to permit inlet flow of blood to the housing, a blood outlet port to permit outlet flow of the blood from the housing, a gas inlet port to permit inlet flow of a gas to the housing, a gas outlet port to permit outlet flow of the gas from the housing, and a plurality of baffles concentrically disposed within the housing. The baffles are positioned to define a flow path between the blood inlet port and the blood outlet port. Each of the baffles includes a gate opening to permit flow of the blood along the flow path. A fiber bundle is disposed between the baffles within the flow create mixing and improve gas exchange efficiency.

16 Claims, 5 Drawing Sheets

(56) References Cited

U.S. PATENT DOCUMENTS

| | | | |
|---|---|---|---|
| 4,220,535 | A | 9/1980 | Leonard |
| 4,919,802 | A | 4/1990 | Katsura |
| 5,169,530 | A | 12/1992 | Schucker et al. |
| 5,352,361 | A | 10/1994 | Prasad et al. |
| 5,651,765 | A * | 7/1997 | Haworth ............. A61M 1/3627 604/6.09 |
| 6,217,826 | B1 | 4/2001 | Reeder et al. |
| 6,454,999 | B1 | 9/2002 | Farhangnia et al. |
| 8,394,049 | B2 | 3/2013 | Reggiani et al. |
| 8,444,586 | B2 | 5/2013 | Beck |
| 2002/0143397 | A1 * | 10/2002 | von Segesser ............ A61F 2/04 623/9 |
| 2005/0025680 | A1 | 2/2005 | Monzyk et al. |
| 2005/0163656 | A1 | 7/2005 | Galavotti |
| 2010/0145471 | A1 | 6/2010 | Johns |
| 2013/0209314 | A1 | 8/2013 | Roller et al. |
| 2014/0030149 | A1 | 1/2014 | Takeuchi |
| 2016/0015881 | A1 | 1/2016 | Utsugida et al. |
| 2017/0258980 | A1 | 9/2017 | Katsuki et al. |

OTHER PUBLICATIONS

International Search Report and Written Opinion for PCT/US2019/037675, dated Oct. 15, 2019.

* cited by examiner

GATED-CONCENTRIC ARTIFICIAL LUNG

CROSS-REFERENCE TO RELATED APPLICATIONS

This application is a U.S. National Phase Application under 35 U.S.C. 371 of International Application No. PCT/US2015/056177 filed on Oct. 19, 2015 and published as WO 2016/064715 A1 on Apr. 28, 2016. This application claims the benefit of U.S. Provisional Application No. 62/065,790, filed on Oct. 20, 2014. The entire disclosure of the above application is incorporated herein by reference.

FIELD

The present disclosure relates to a unique design for an artificial lung, featuring a series of concentric compartments separated by precisely placed gates.

BACKGROUND AND SUMMARY

This section provides background information related to the present disclosure which is not necessarily prior art. This section provides a general summary of the disclosure, and is not a comprehensive disclosure of its full scope or all of its features.

Chronic obstructive pulmonary disease (COPD) is the third leading cause of death in the United States. For end-stage COPD, lung transplantation is the only curative therapy available at this time. The demand for lungs, however, exceeds the donor supply, resulting in long wait-times and ineligibility. An oxygenator that is driven entirely by the heart and designed to provide pulmonary support, primarily by clearance of carbon dioxide, is a promising alternative for end-stage COPD patients waiting for or ineligible for lung transplantation. The effectiveness and life span of such an oxygenator can be greatly increased by generating secondary flows, which enhance the mixing of blood, thereby reducing thrombogenecity and improving efficiency of gas transport. The efficiency of an oxygenator can be further increased by having a relatively short gas path, which will reduce the buildup of carbon dioxide in the ventilating gas and thereby increase the gradient for carbon dioxide clearance.

In view of the foregoing, it is the objective of the present teachings to provide a pumpless concentric artificial oxygenator, driven by external perfusion, having a compact size, low priming volume, and the ability to adequately remove carbon dioxide from and oxygenate blood using a short gas path and a plurality of single-gated baffles with specific placements that passively generate orderly secondary flows and recirculation, enhancing the mixing of blood and thereby reducing thrombogenecity and improving efficiency of gas exchange.

This concentric artificial oxygenator technology of the present teachings (also synonymously called an artificial lung, prosthetic lung, oxygenator, membrane oxygenator, and the like—these terms may be used interchangeably herein) can be used to oxygenate blood and remove carbon dioxide ($CO_2$) in heart-lung machines including extracorporeal devices (ECMO). In this application, the artificial lung can be used for patients requiring heart operations and support for acute heart and/or lung failure. A heart-lung machine is used for one million patients per year in the United States. Thus, this technology can help a significant patient population.

This technology uses gated spiral flow of the blood which results in secondary flow to increase oxygenation. The secondary flow results in increased mixing which improves oxygenation. The formation of blood clots (thrombus) is a major problem that limits the use of heart-lung machines and extracorporeal membrane oxygenation (ECMO) to a few hours and a few weeks, respectively. This technology reduces the tendency to form blood clots and extends the time that patients can be managed using a prosthetic lung. This technology may also act as a bridge to transplant for lung transplant candidates whom are adversely affected by the limited supply of donor lungs. This technology can significantly improve surgical and intensive care outcomes.

In summary, the present teachings provide an artificial lung having a plurality of baffles in the blood phase to create mixing and improve gas exchange efficiency. The lung is designed for use as an implantable or wearable device driven by the patient's native circulation and can also be used with a pump in a heart-lung machine.

In some embodiments, the artificial lung of the present teachings is a hollow fiber membrane lung with concentric baffles in the blood flow path designed to increase mixing and thereby increase the efficiency of gas exchange, and to minimize stagnation thereby minimizing clotting in the artificial lung of the present teachings. The artificial lung of the present teachings has low blood flow resistance permitting perfusion via the pulmonary artery or via a peripheral artery, such as the subclavian artery. This resistance is achieved by the placement and size of the gates in the baffles and by modifying the density of the fiber bundle. In some embodiments, the resistance ranges from 10 to 30 mmHg per liter of blood flow, depending on the size and intended application of the artificial lung of the present teachings.

In some embodiments, the artificial lung of the present teachings achieves minimal or no thrombogenicity in light of its unique design and configuration. For example, in some embodiments, the artificial lung is capable of minimizing clotting and platelet activation due to its increased gas transfer efficiency per membrane surface area that leads to short transit times. The artificial lung minimizes or eliminates stagnation of blood due to the design of the baffles and the position and the size of the gates. This design results in no increased shear stress that may cause platelet activation. Moreover, the hard surface components of the artificial lung of can be coated with nonthrombogenic material to further aid in minimal thrombogenicity.

In some embodiments, the artificial lung of the present teachings comprises a housing having a circular outer wall being enclosed by a first surface and a second surface to define an interior volume, a blood inlet port to permit inlet flow of blood to the housing, a blood outlet port to permit outlet flow of the blood from the housing, a gas inlet port to permit inlet flow of a gas to the housing, a gas outlet port to permit outlet flow of the gas from the housing, and a plurality of baffles concentrically disposed within the housing. The baffles are positioned to define a flow path between the blood inlet port and the blood outlet port. Each of the baffles includes one or more gate openings to permit flow of the blood along the flow path. A fiber bundle is disposed between the baffles within the flow create mixing and improve gas exchange efficiency.

In some embodiments, the size, shape, and resistance of the artificial lung of the present teachings are designed for implantable or wearable placement and application (although the artificial lung of the present teachings can be perfused with a pump, if desired).

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1A:
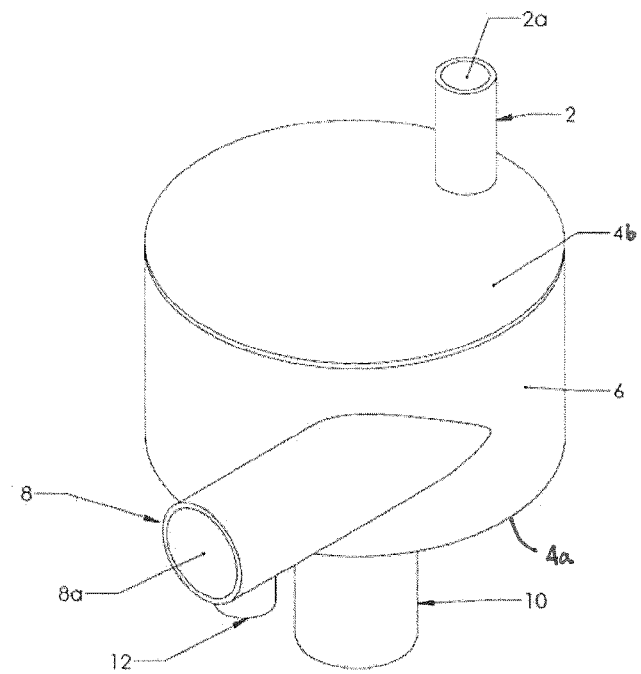
FIG. 1A is a perspective view illustrating a gated-concentric artificial lung according to the principles of the present teachings.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Device Configuration

The present teachings provide a concentric artificial oxygenator, driven by external perfusion, having a compact size, low priming volume, and the ability to adequately remove carbon dioxide from and oxygenate blood using a plurality of single-gated baffles with specific placements that passively generate orderly secondary flows and recirculation, enhancing the mixing of blood and thereby reducing thrombogenecity and improving efficiency of gas exchange. Furthermore, the present teachings feature a short gas path, e.g. 4 inches or less, which will reduce the buildup of carbon dioxide in the ventilating gas and thereby increase the gradient for carbon dioxide clearance.

The specific patterns of secondary flows generated depend on a variety of factors, including inlet flow rate. Since the inlet flow rate is dependent on the cardiac output and arterial and venous pressures of individual patients, the configuration of the present teachings may vary, namely: the number and placements of the baffles, gate opening width, dimensions of the blood inlet and outlet, height of the device, and fiber packing density.

Referring to FIGS. 1A, 1B, 2, 3A, and 3B, a spiral gated membrane lung 1 in accordance with the principles of the present teachings is shown. The device 1 has a housing 6 comprising a blood inlet port 8, blood outlet port 10, gas inlet port 12, gas outlet port 2, and lid 4. Deoxygenated blood enters the blood inlet port lumen 8a via suitable biocompatible tubing (not shown) connected to the blood inlet port 8, and oxygenated blood exits the oxygenator through the blood outlet port 10. In some embodiments, air with a high oxygen and low carbon dioxide concentration is introduced in via gas inlet port 12 and a mixture of low oxygen and high carbon dioxide concentrations exits the oxygenator via gas outlet port lumen 2a. In some embodiments, this air or "sweep gas" can be ambient air, if the application is $CO_2$ removal, or 100% oxygen, if the application is oxygenation.

Figure 1B:
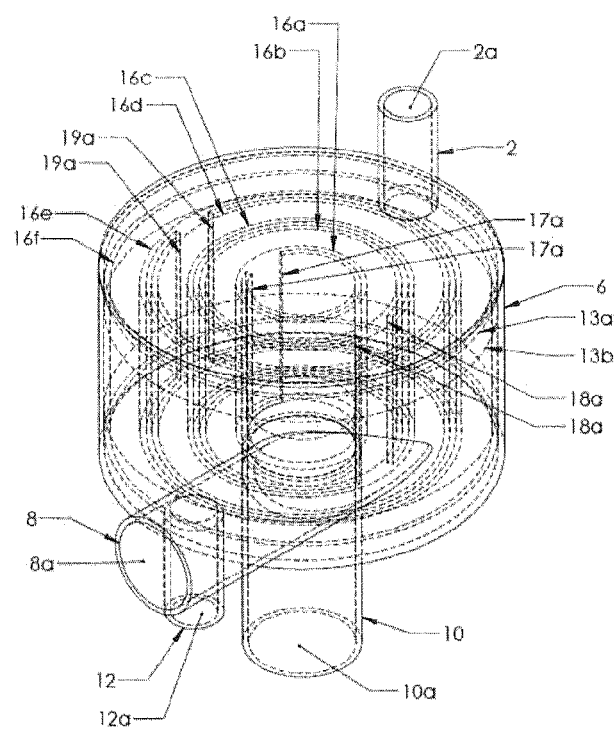
FIG. 1B is a perspective view illustrating the gated-concentric artificial lung in phantom.
Figure 2:
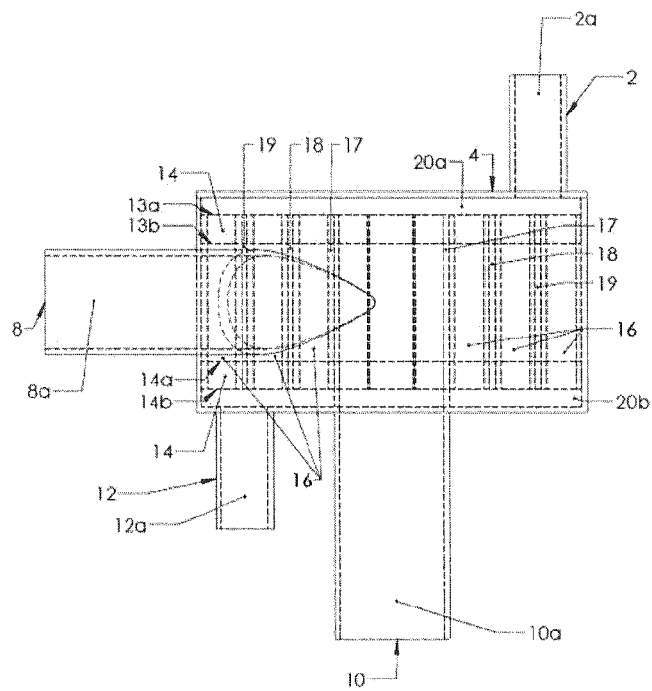
FIG. 2 is a side view illustrating the gated-concentric artificial lung in phantom.
Figure 3A:
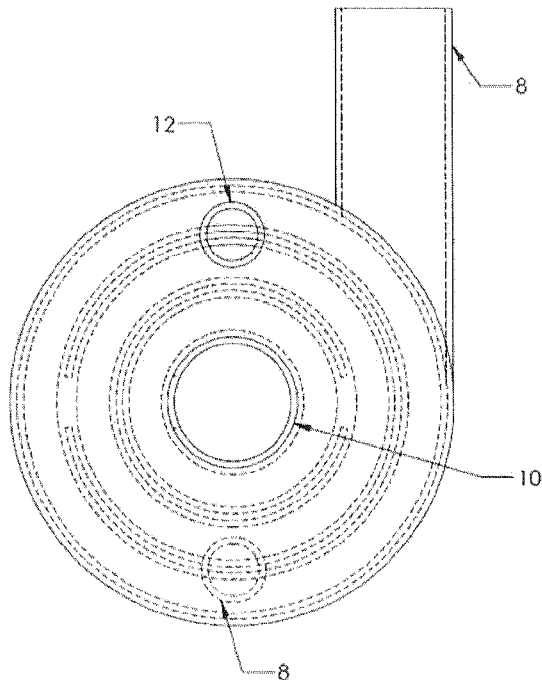
FIG. 3A is a top view illustrating the gated-concentric artificial lung in phantom.
Figure 3B:
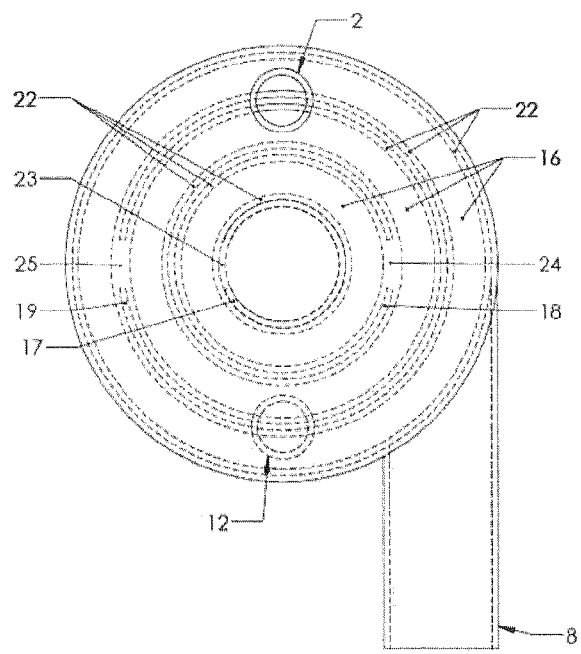
FIG. 3B is a bottom view illustrating the gated-concentric artificial lung in phantom.

As shown in FIGS. 1B and 2, the housing 6 encloses a fiber bundle 16 and a plurality of concentrically-disposed circular dividers or baffles 17-19 radially separating the fiber bundle 16.

Each baffle 17-19 has one or more gate openings 23-25, allowing the blood to flow through the fiber bundle 16 compartments: the blood from the blood inlet port 8 flows through the outermost fiber bundle compartment, outlined by 16e and 16f; into the second outermost fiber bundle compartment, outlined by 16c and 16d; via the outermost gate 25. The blood from the second outermost fiber bundle compartment, outlined by 16c and 16d, then flows through the second outermost gate 24 into the third outermost fiber bundle compartment, outlined by 16a and 16c. Next, the blood from the third outermost fiber bundle compartment, outlined by 16a and 16b, flows through the third outermost gate 23 into the lumen of the blood outlet port 10a. An illustration of the baffles with the gate openings is shown in FIGS. 5A-5D. The width of each gate is the distance between the edges of the opening arc of the baffle placed at a given radial distance; the widths of gates 23, 24, and 25 are the distances between the edges of the opening arc of baffles shown by 17a, 18a, and 19a, respectively. The innermost baffle 17 includes an extension 17b (see FIG. 5D) that creates a path for the blood to flow from the innermost gate 23 to the blood outlet lumen 10a.

The specific pattern of secondary flows generated depends on a variety of factors, including inlet flow rate and pulsatility and the specific configuration of baffles and gates. Since the inlet flow rate and pulsatility is dependent on the cardiac output and arterial and venous pressures of individual patients, the present teachings may include a plurality of baffle and gate configurations, in which fewer than or more than 3 baffles placed a various radial distances may be used, and gates at each baffle may have a variety of gate widths, based on individual patient needs.

Figure 4A:
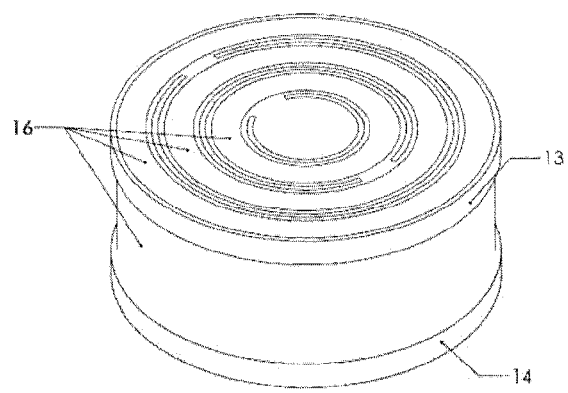
FIG. 4A is a perspective view illustrating the gated-concentric artificial lung.
Figure 4B:
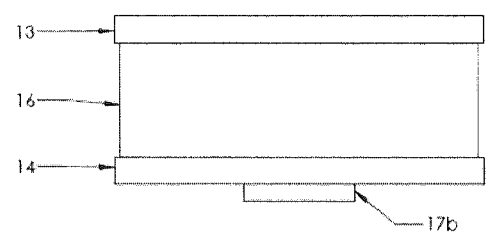
FIG. 4B is a side view illustrating the gated-concentric artificial lung.
Figure 4C:
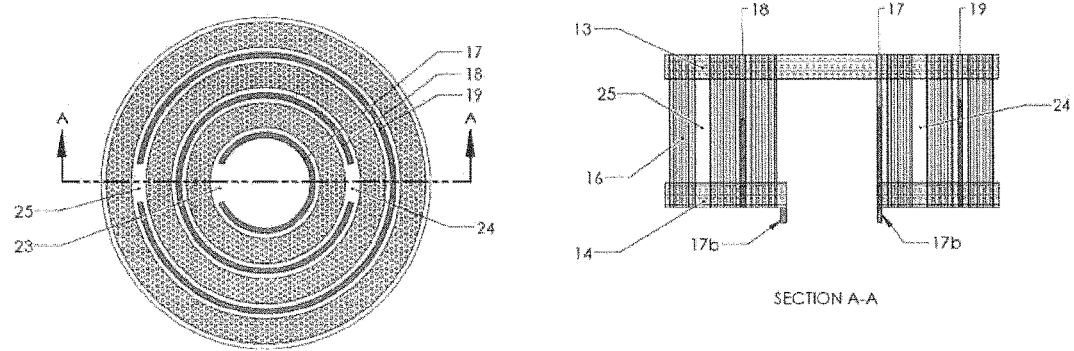
FIG. 4C is a side cross-sectional view illustrating the gated-concentric artificial lung.
Figure 5A:
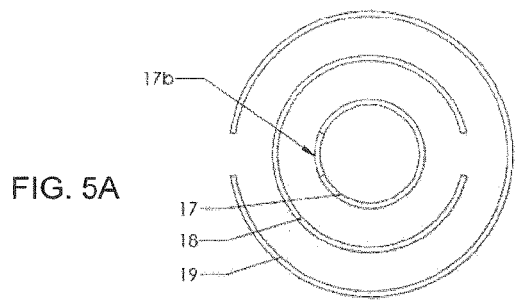
FIG. 5A is a top partition view illustrating the gated-concentric artificial lung.
Figure 5B:
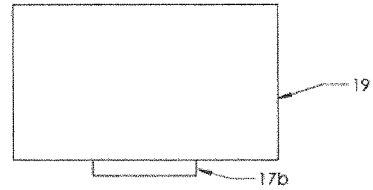
FIG. 5B is a side partition view illustrating the gated-concentric artificial lung.
Figure 5C:
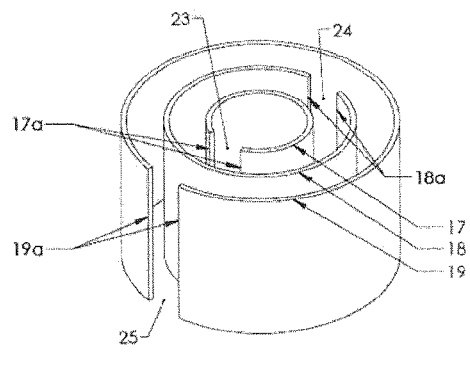
FIG. 5C is a perspective partition view illustrating the gated-concentric artificial lung.
Figure 5D:
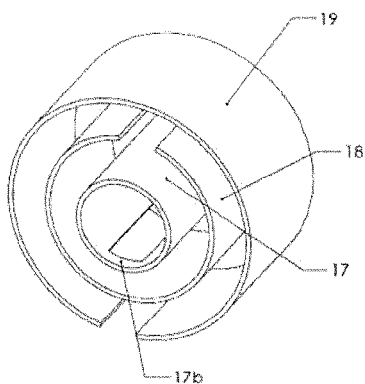
FIG. 5D is another perspective partition view illustrating the gated-concentric artificial lung.

FIGS. 4A-4C show the baffles 17-19 coupled with the fiber bundle 16. The fiber bundle 16 preferably comprises a multiplicity of microporous hollow fibers having upper ends potted at the region enclosed by 13a and 13b, so that the interior lumens of the fibers communicate with plenum 20a. Similarly, the lower ends are potted at the region enclosed by 14a and 14b, so that the interior lumens of the fibers communicate with plenum 20b. Any number of suitable biocompatible potting materials, such as polyurethanes or epoxies, may be used for the potted regions 13,14. The fiber bundle 16 is wound around the innermost baffle 17 such that the cross section of each fiber is parallel to the lid 4.

In some embodiments, as illustrated in the figure, blood inlet port 8 is at the periphery of housing 6, such that blood enters inlet port lumen 8a at a tangent to the housing 6. The blood then flows through the fiber bundle 16 directed by the baffles 17, 18, 19 and exits at the center of the artificial lung at the blood outlet port 10. This blood flow path is intended to enhance mixing by running counter current to the normal centrifugal force which would drive the blood from the center to the edge when the blood is introduced in the center. This additional feature increases gas transfer efficiency and minimizes thrombosis.

The geometry and efficiency of hollow fiber membrane lungs is described by the concept "rated flow." The rated flow is that flow of normal venous blood which can be oxygenated to 95% saturation during a single pass through the artificial lung. The rated flow of the gated concentric artificial lung of the present teachings will depend on the size, which in turn depends on the application to specific patients. For example, a membrane lung for infants (1-10 kg) is designed to have a rated flow 1 L/min supplying 5-50 cc oxygen per minute. A membrane lung for pediatrics (10-30 kg) is designed to have a rated flow 1-3 L/min supplying 50-150 cc oxygen per minute. A membrane lung for adults (30-100 kg) is designed to have a rated flow 3-6 L/min supplying 150-300 cc oxygen per minute.

Flow Discussion

Normal laminar flow of blood occurs when blood passes through a gas exchange device, so that most of the red cells do not come into contact with the gas exchange surface. Efficiency is achieved by disrupting the laminar flow, bringing red cells to the gas exchange surface. The artificial lung of the present teachings interrupts the laminar flow by radial flow across the fiber bundle 16. The blood contacting each hollow fiber of the fiber bundle 16 is disrupted so that each red cell is mixed and brought to a gas exchange surface in the process of blood passing through the artificial lung.

Conventional hollow fiber membrane lungs achieve disruption of laminar flow by the passage of blood from a central point to a peripheral point crossing through a fiber bundle. In the artificial lung of the present teachings that flow is intentionally disrupted by the series of baffles which are designed to maximize mixing and minimize thrombosis. It is important that the blood flow be directed across the fiber bundles 16 rather than in parallel with the fibers. The disruption of laminar flow is significant but is short of inducing turbulent flow (Reynolds numbers over 1,000).

In addition, blood flowing around a curve generates secondary flows, which enhances mixing. In the artificial lung of the present teachings, all the blood flow channels are all curved (in fact, circular) to generate secondary flows in the flowing blood.

Development Summary

Figures 6A, 6B:
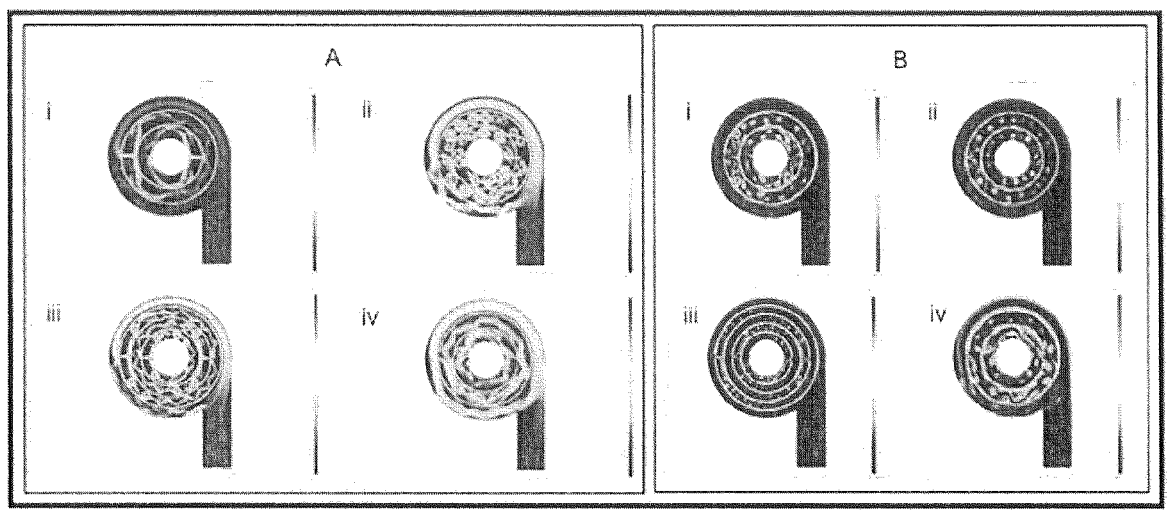
FIGS. 6A and 6B illustrate the gated-concentric artificial lung in operation.

The development plan for the present teachings is as follows: first, one may optimize the configuration of the present design, such as gate, baffle, and inlet/outlet placement, by carrying out a finite element analysis using computational fluid dynamics (CFD). The resulting CFD velocity and vorticity profiles for the proposed TAL design show a significant increase in secondary flows. FIGS. 6A and 6B shows various representative velocity and vorticity profiles generated by a 1 Hz pulsatile inlet flow with an average flow rate of 3 L min-1. Decreasing gate width results in more fully developed vortices (FIG. 6A [ii, iv] and 6B [ii, iv]), while increasing the number of gates results in an effectively longer fluid path length and a higher number of vortices with smaller radii (FIG. 6A [ii, iii] and 6B [ii, iii]). The mixing was quantified by evaluating the vorticity and circulation through the device, while the simultaneous pressure, resistance, and shear stresses were evaluated to ensure that the blood flowing through the optimized design configuration was below the thresholds for blood trauma. Once a primary iteration of the optimized design was identified, a prototype of the present teachings without fibers was built using stereolithography, and CFD results were verified using particle image velocimetry (PIV) studies. Next, the CFD model was modified to include fiber bundling, and the design was further optimized for enhanced flow mixing, low resistance, and low shear rates.

It has been found that the present teachings provide reduced thrombosis and more efficient gas transfer as a result of the orderly secondary flows generated. Further, as a pumpless oxygenator driven entirely by the heart, it has shown the potential to serve as a wearable, long-term treatment for end-stage COPD patients.

The present teachings further provide a passive membrane oxygenator that results in a specific flow pattern with vortexes, determined by the exact placement and size of the single gate at each circumferential divide. None of the currently available oxygenator setups of which use baffles or gates, designed to interrupt flow or increase recirculation, shows a flow pattern as seen in FIG. 6 of the present teachings. It is noteworthy that the only conventional designs that demonstrate a flow pattern with clear vortexes forming are in designs that have a rotating or pumping component. Therefore, it is not an obvious prediction that the gated spiral device, with no rotating/pumping component, would result in the specific flow pattern with vortex formation as seen.

SUMMARY

In summary, as described herein and illustrated in the figures, the artificial lung 10 of the present teaches can comprise:

a housing 6 having a circular outer wall being enclosed by a first surface 4a and a second surface 4b to define an interior volume;

a blood inlet port 8 operable to permit inlet flow of blood to the interior volume of the housing 6;

a blood outlet port 10 operable to permit outlet flow of the blood from the interior volume of the housing 6;

a gas inlet port 12 operable to permit inlet flow of a gas to the interior volume of the housing 6;

a gas outlet port 2 operable to permit outlet flow of the gas from the interior volume of the housing 6;

a plurality of baffles 17, 18, 19 concentrically disposed within the housing 6, the plurality of baffles being positioned to define a flow path between the blood inlet port 8 and the blood outlet port 10, each of the plurality of baffles includes a gate opening 23, 24, 25 formed therethrough to permit flow of the blood along the flow path; and a fiber bundle 16 being disposed within the housing 6 and between the plurality of baffles 17, 18, 19 within the flow path such that the blood flows along the flow path through the fiber bundle 16 and gate openings 23, 24, 25 from the blood inlet port 8 to the blood outlet port 10.

In some embodiments, the plurality of baffles, the size and number of gate openings, and the fiber bundle are selected to maintain a non-turbulent blood flow along the flow path having a Reynolds number less than 1000.

In some embodiments, the inlet flow of blood to the interior volume of the housing via the blood inlet port is provided solely based on a patient's native circulatory system.

In some embodiments, the first surface of the housing is a removable lid.

In some embodiments, the blood inlet port is directed at a tangent position relative to the circular outer wall of the housing. In some embodiments, the blood inlet port is directed at two or more tangent positions relative to the circular outer wall of the housing.

In some embodiments, the blood inlet port is disposed through the circular outer wall of the housing.

In some embodiments, the blood outlet port is disposed coaxially at a central longitudinal axis of the housing.

In some embodiments, the blood outlet port is disposed through the first surface of the housing.

In some embodiments, the gas inlet port is also disposed through the first surface of the housing.

In some embodiments, the gas outlet port is disposed through the second surface of the housing.

In some embodiments, the flow path is generally in a direction from a peripheral section of the housing to a central section of the housing.

In some embodiments, each of the plurality of baffles is discrete relative to the remaining plurality of baffles. That is, each of the plurality of baffles may be non-intersecting with adjacent baffles.

In some embodiments, a gate opening of a first of the plurality of baffles is radially offset relative to a gate opening of a second of the plurality of baffles. In this way, gate openings within adjacent baffles will not be aligned, thereby requiring the blood to flow along the flow path.

In some embodiments, a gate opening of a third of the plurality of baffles is radially aligned relative to the gate opening of the first of the plurality of baffles.

In some embodiments, each of the plurality of baffles is circularly shaped to define a circular flow path.

In some embodiments, wherein the plurality of baffles are fixedly coupled to at least one of the first surface and the second surface of the housing.

In some embodiments, wherein the fiber bundle is configured to encourage the blood to flow in a direct across the fiber bundle.

In some embodiments, wherein the fiber bundle is coupled to the first surface and the second surface.

In some embodiments, wherein the fiber bundle defines a flow resistance in the range of 10 mmHg to 30 mmHg per liter of blood flow.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An artificial lung comprising:
a housing having a circular outer wall being enclosed by a first surface and a second surface to define an interior volume;
a blood inlet port operable to permit inlet flow of blood to the interior volume of the housing; a blood outlet port operable to permit outlet flow of the blood from the interior volume of the housing;

a gas inlet port operable to permit inlet flow of a gas to the interior volume of the housing;

a gas outlet port operable to permit outlet flow of the gas from the interior volume of the housing;

a plurality of baffles concentrically disposed within the housing and fixedly coupled to the housing, the plurality of baffles being positioned to define a flow path between the blood inlet port and the blood outlet port, each of the plurality of baffles includes a gate opening formed therethrough to permit flow of the blood along the flow path; and a non-rotating fiber bundle being disposed within and fixedly coupled to the housing and between the plurality of baffles within the flow path, the non-rotating fiber bundle being configured to passively generate orderly secondary flows and recirculation as the blood flows along the flow path through the non-rotating fiber bundle and gate openings from the blood inlet port to the blood outlet port, wherein the inlet flow of blood to the interior volume of the housing via the blood inlet port is provided solely based on a patient's native circulatory system.

2. The artificial lung according to claim 1 wherein the plurality of baffles, the gate openings, and the non-rotating fiber bundle are selected to maintain a non-turbulent blood flow along the flow path having a Reynolds number less than 1000.

3. The artificial lung according to claim 1 wherein the blood inlet port is directed at a tangent position relative to the circular outer wall of the housing.

4. The artificial lung according to claim 1, further comprising:

a second blood inlet port directed at a second tangent position relative to the circular outer wall of the housing.

5. The artificial lung according to claim 1 wherein the blood inlet port is disposed through the circular outer wall of the housing.

6. The artificial lung according to claim 1 wherein the blood outlet port is disposed coaxially at a central longitudinal axis of the housing.

7. The artificial lung according to claim 1 wherein the blood outlet port is disposed through the first surface of the housing.

8. The artificial lung according to claim 1 wherein the gas inlet port is disposed through the first surface of the housing.

9. The artificial lung according to claim 1 wherein the gas outlet port is disposed through the second surface of the housing.

10. The artificial lung according to claim 1 wherein the flow path is generally in a direction from a peripheral section of the housing to a central section of the housing.

11. The artificial lung according to claim 1 wherein each of the plurality of baffles is discrete relative to the remaining plurality of baffles.

12. The artificial lung according to claim 1 wherein a gate opening of a first of the plurality of baffles is radially offset relative to a gate opening of a second of the plurality of baffles.

13. The artificial lung according to claim 12 wherein a gate opening of a third of the plurality of baffles is radially aligned relative to the gate opening of the first of the plurality of baffles.

14. The artificial lung according to claim 1 wherein each of the plurality of baffles is circularly shaped to define a circular flow path.

15. The artificial lung according to claim 1 wherein the fiber bundle is configured to encourage the blood to flow in a direct across the fiber bundle.

16. The artificial lung according to claim 1 wherein the fiber bundle defines a flow resistance in the range of 10 mmHg to 30 mmHg per liter of blood flow.

* * * * *